US009888854B2

(12) United States Patent
Sato (10) Patent No.: US 9,888,854 B2
(45) Date of Patent: Feb. 13, 2018

(54) BIOMETRIC DEVICE, BIOMETRIC METHOD, PROGRAM, AND RECORDING MEDIUM

(75) Inventor: Hideo Sato, Tokyo (JP)

(73) Assignee: Sony Corporation (JP)

(*) Notice: Subject to any disclaimer, the term of this patent is extended or adjusted under 35 U.S.C. 154(b) by 197 days.

(21) Appl. No.: 14/356,997

(22) PCT Filed: Aug. 22, 2012

(86) PCT No.: PCT/JP2012/071222
§ 371 (c)(1),
(2), (4) Date: May 8, 2014

(87) PCT Pub. No.: WO2013/073245
PCT Pub. Date: May 23, 2013

(65) Prior Publication Data
US 2014/0296668 A1 Oct. 2, 2014

(30) Foreign Application Priority Data

Nov. 16, 2011 (JP) ................. 2011-250997

(51) Int. Cl.
*A61B 5/1455* (2006.01)
*A61B 5/00* (2006.01)
(Continued)

(52) U.S. Cl.
CPC .......... *A61B 5/0071* (2013.01); *A61B 5/1455* (2013.01); *G01J 3/021* (2013.01);
(Continued)

(58) Field of Classification Search
CPC .............. A61B 5/1455; A61B 5/14551; A61B 5/14552; A61B 2562/0233
See application file for complete search history.

(56) References Cited

U.S. PATENT DOCUMENTS 6,124,597 A * 9/2000 Shehada .............. A61B 5/0075
600/323
7,139,598 B2 * 11/2006 Hull ...................... A61B 5/1455
600/310
(Continued)

FOREIGN PATENT DOCUMENTS

JP 11-037938 2/1999
JP 2004-344668 A 12/2004
(Continued)

OTHER PUBLICATIONS

Kiyotaka Sasagawa et al., "Implantable CMOS image sensors for monitoring brain activities", Function & materials, Jan. 5, 2011 (Jan. 5, 2011), vol. 31, No. 2, pp. 24 to 32 (Concise explanation of relevance provided in the ISR of Nov. 27, 2011).
(Continued)

*Primary Examiner* — Eric Winakur
(74) *Attorney, Agent, or Firm* — Lerner, David, Littenberg, Krumholz & Mentlik, LLP (57) ABSTRACT

Provided is a biometric device including a light source unit arranged facing a first part on a surface of an organism and configured to irradiate the first part with excitation light, and a light-reception unit arranged facing a second part adjacent to the first part on the surface of the organism and configured to receive fluorescence light which is generated by the excitation light exciting a first body substance of the organism and emitted from the second part.

6 Claims, 9 Drawing Sheets

(51) Int. Cl.
- *G01N 21/64* (2006.01)
- *G01J 3/44* (2006.01)
- *G01J 3/02* (2006.01)
- *G01J 3/14* (2006.01)
- *G01J 3/36* (2006.01)
- *G01J 3/12* (2006.01)

(52) U.S. Cl.
CPC ........... *G01J 3/0202* (2013.01); *G01J 3/0208* (2013.01); *G01J 3/14* (2013.01); *G01J 3/36* (2013.01); *G01J 3/44* (2013.01); *G01N 21/645* (2013.01); *G01N 21/6486* (2013.01); *G01J 2003/1213* (2013.01); *G01N 2021/6421* (2013.01); *G01N 2021/6471* (2013.01)

(56) References Cited

U.S. PATENT DOCUMENTS

| | | | |
|---|---|---|---|
| 7,643,860 | B2 | 1/2010 | Gueissaz |
| 7,786,443 | B2 | 8/2010 | Peter et al. |
| 8,227,754 | B2 | 7/2012 | Peter et al. |
| 8,581,697 | B2 | 11/2013 | Ridder et al. |
| 8,686,376 | B2 | 4/2014 | Wimberger-Friedl et al. |
| 2002/0016534 | A1* | 2/2002 | Trepagnier ........... A61B 5/1455 600/316 |
| 2011/0164249 | A1 | 7/2011 | Innami et al. |

FOREIGN PATENT DOCUMENTS

| | | |
|---|---|---|
| JP | 2005-227155 A | 8/2005 |
| JP | 2006-112839 A | 4/2006 |
| JP | 2007-510159 A | 4/2007 |
| JP | 2008-538312 A | 10/2008 |
| JP | 2011-097986 A | 5/2011 |
| JP | 2011-525629 A | 9/2011 |
| WO | WO01/22869 * | 4/2001 |

OTHER PUBLICATIONS

Sasagawa K, et. al., Implantable Image Sensor with Light Guide Array Plate for Bioimaging, Japanese Journal of Applied Physics, Apr. 25, 2010, vol. 49, No. 4, Issue 2, pp. 04DL03.1-040103.5.
International Search Report dated Nov. 27, 2011.
Kiyotaka Sasagawa et al., "Implantable CMOS image sensors for monitoring brain activities", Function & materials, Jan. 5, 2011 (Jan. 5, 2011), vol. 31, No. 2, pp. 24 to 32.

* cited by examiner

BIOMETRIC DEVICE, BIOMETRIC METHOD, PROGRAM, AND RECORDING MEDIUM

CROSS-REFERENCE TO RELATED APPLICATION

The present application is a national phase entry under 35 U.S.C. § 371 of International Application No. PCT/JP2012/071222 filed Aug. 22, 2012, published on May 23, 2013 as WO 2013/073245 A1, which claims priority from Japanese Patent Application No. JP 2011-250997, filed in the Japanese Patent Office on Nov. 16, 2011.

TECHNICAL FIELD

The present disclosure relates to a biometric device, a biometric method, a program, and a recording medium.

BACKGROUND ART

In recent years, technologies for non-invasively carrying out biometric measurements using optics have been developed. In these technologies, in addition to Raman spectroscopy or near infrared spectroscopy and the like, for example, fluorescence spectroscopy for measuring fluorescence light generated by excitation light such as ultraviolet rays applied to an organism is also utilized. Examples of biometric technologies using the fluorescence spectroscopy are described in Patent Literature 1, for example.

CITATION LIST

Patent Literature

Patent Literature 1: JP 2007-510159T

SUMMARY OF INVENTION

Technical Problem

However, in the biometric technologies using the fluorescence spectroscopy as described above, in order to irradiate an entire target region of the organism with the excitation light, a space is needed between a source of excitation light and an organism. In addition, a certain distance is also needed between a light-reception unit of fluorescence light and the organism to receive the fluorescence light from the entire target region. Therefore, it was difficult to downsize a device for biometric measurement.

Hence, in the present disclosure, a new and improved biometric device, biometric method, program and recording medium which can downsize the device for biometric measurement using the fluorescence spectroscopy are proposed.

Solution to Problem

According to the present disclosure, there is provided a biometric device including a light source unit arranged facing a first part on a surface of an organism and configured to irradiate the first part with excitation light, and a light-reception unit arranged facing a second part adjacent to the first part on the surface of the organism and configured to receive fluorescence light which is generated by the excitation light exciting a first body substance of the organism and emitted from the second part.

According to the present disclosure, there is provided a biometric method including irradiating a first part on a surface of an organism with excitation light, and receiving fluorescence light which is generated by the excitation light exciting a first body substance of the organism and emitted from a second part adjacent to the first part on the surface of the organism.

According to the present disclosure, there is provided a program for causing a computer included in a biometric device including a light source unit and a light-reception unit to implement a function of controlling the light source unit, and a function of controlling the light-reception unit, the light source unit being arranged facing a first part on a surface of an organism and being configured to irradiate the first part with excitation light, the light-reception unit being arranged facing a second part adjacent to the first part on the surface of the organism and being configured to receive fluorescence light which is generated by the excitation light exciting a first body substance of the organism and emitted from the second part.

According to the present disclosure, there is provided a computer-readable recording medium having a program recorded thereon, the program causing a computer included in a biometric device including a light source unit and a light-reception unit to implement a function of controlling the light source unit, and a function of controlling the light-reception unit, the light source unit being arranged facing a first part on a surface of an organism and being configured to irradiate the first part with excitation light, the light-reception unit being arranged facing a second part adjacent to the first part on the surface of the organism and being configured to receive fluorescence light which is generated by the excitation light exciting a first body substance of the organism and emitted from the second part.

According to the present disclosure, there is provided a biometric device including a light source unit arranged facing a first part on a surface of an organism and configured to apply excitation light in a direction inclined to the surface of the organism, and a light-reception unit arranged facing a second part adjacent to the first part on the surface of the organism and configured to receive fluorescence light in a direction substantially perpendicular to the surface of the organism, the fluorescence light being generated by the excitation light exciting a first body substance of the organism and emitted from the second part. A direction in which the excitation light is applied is substantially orthogonal to the direction of the fluorescence light.

According to the configurations of the present disclosure described above, the light source unit and the light-reception unit are arranged in separate parts on the surface of the organism. Therefore, a space between the light source unit and the light-reception unit and the organism may be small, which thus enables downsizing of the device.

Advantageous Effects of Invention

As described above, according to the present invention, a device for biometric measurement using the fluorescence spectroscopy can be downsized.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

Note that descriptions will be given in the following order:
1. Description of related art
2. Embodiments of the present disclosure
   2-1. First embodiment
   2-2. Second embodiment
   2-3. Third embodiment
   2-4. Fourth embodiment
   2-5. Fifth embodiment
   2-6. Sixth embodiment
3. Supplement

1. DESCRIPTION OF RELATED ART

Figure 1:
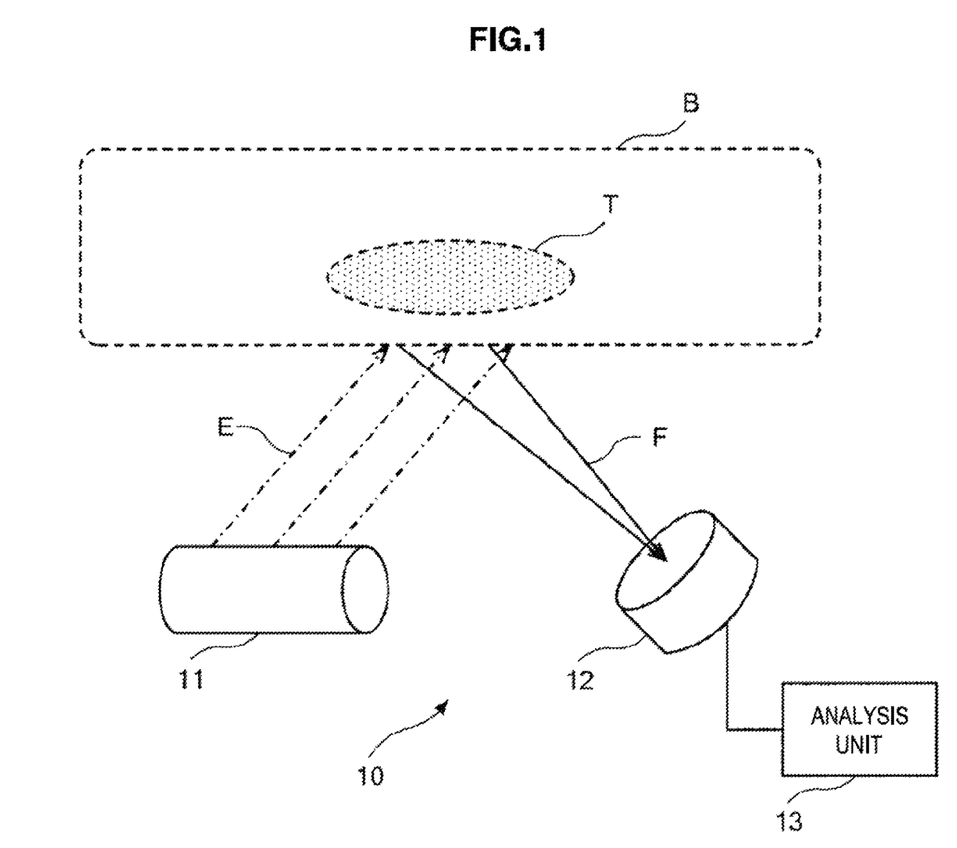
FIG. 1 is an illustration showing a configuration of a biometric device according to related art of embodiments of the present disclosure.

First, the art related to embodiments of the present disclosure will be described with reference to FIG. 1. FIG. 1 is an illustration showing a configuration of a biometric device according to the related art of the embodiments of the present disclosure.

With reference to FIG. 1, a biometric device 10 includes a light source unit 11, a light-reception unit 12, and an analysis unit 13. The biometric device 10 is a biometric device which performs biometric measurements by using the fluorescence spectroscopy. The light source unit 11 irradiates a measurement target part on a surface of an organism B with excitation light E. Fluorescence light F is generated from a body substance T by the excitation light E incident to the organism B exciting the body substance T of the organism B. The light-reception unit 12 receives the fluorescence light F emitted from the measurement target part. The analysis unit 13 quantifies the body substance T by analyzing a spectrum or intensity of the fluorescence light F received by the light-reception unit 12.

In the aforementioned biometric device 10, a certain space is needed between the light source unit 11 and the organism B so that the light source unit 11 can irradiate the entire measurement target part on the surface of the organism B with the excitation light E. In addition, a certain space is also needed between the light-reception unit 12 and the organism B so that the light-reception unit 12 can receive the fluorescence light F from the entire measurement target part on the surface of the organism B. Consequently, the biometric device 10 has become large-size just for the space between the light source unit 11 and the light-reception unit 12 and the organism B, which thus has made downsizing difficult.

In addition, in the biometric device 10, some of the excitation light E applied from the light source unit 11 is reflected on the surface of the organism B and received by the light-reception unit 12 with the fluorescence light F. Specifically, components of the excitation light E are mixed into an analysis result of the fluorescence light F as noise. Since a difference in wavelengths between the excitation light E and the fluorescence light F is relatively small, it has been difficult in the biometric device 10 to separate the excitation light E from the fluorescence light F and receive the fluorescence light F.

Hereinafter, some of the embodiments of the present disclosure will be described. Some advantages of these embodiments will be understood more easily through a comparison with the biometric device according to the related art described above.

2. EMBODIMENTS OF THE PRESENT DISCLOSURE 2-1. First Embodiment

Figure 2:
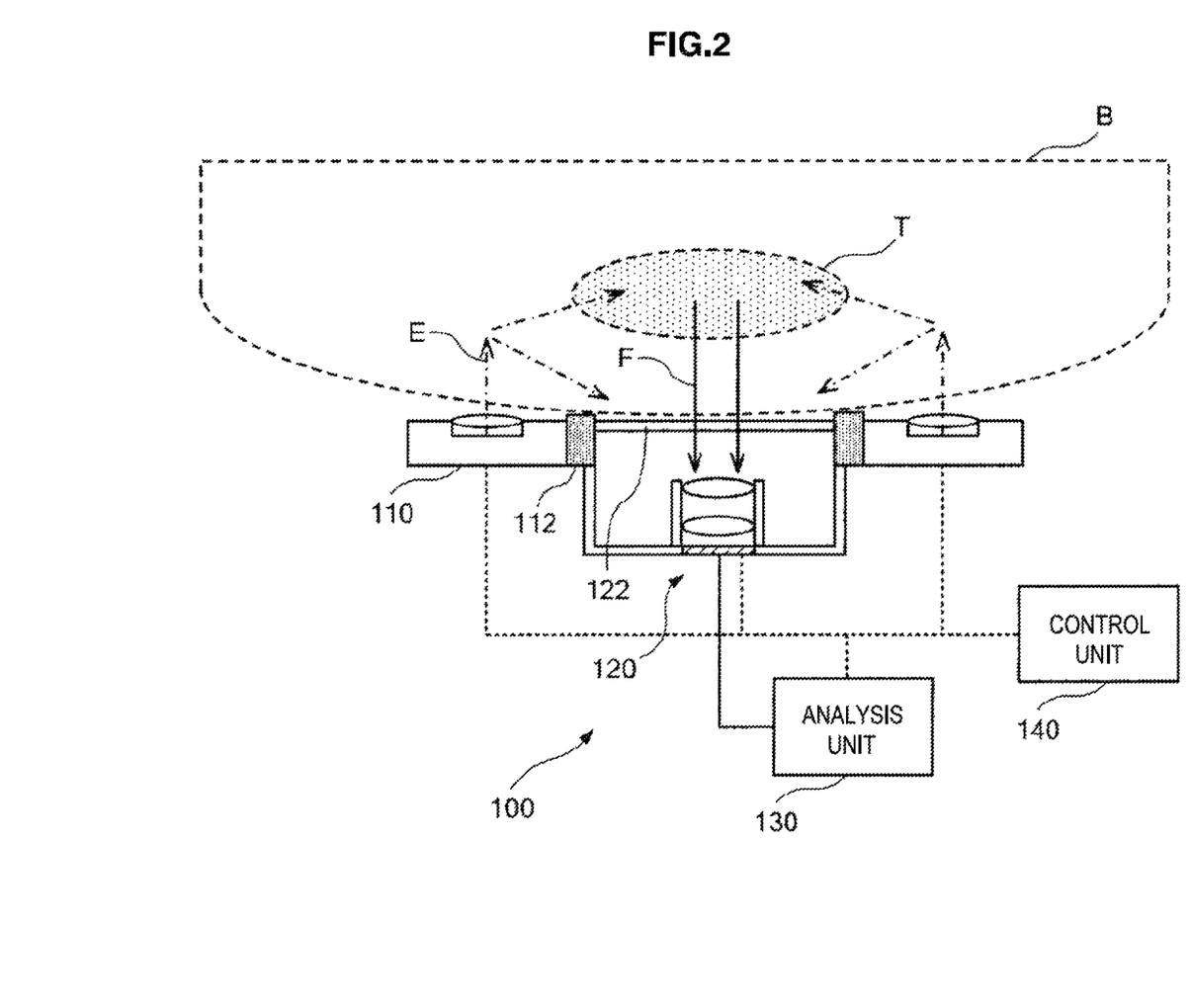
FIG. 2 is an illustration showing a configuration of a biometric device according to a first embodiment of the present disclosure.
Figure 3:
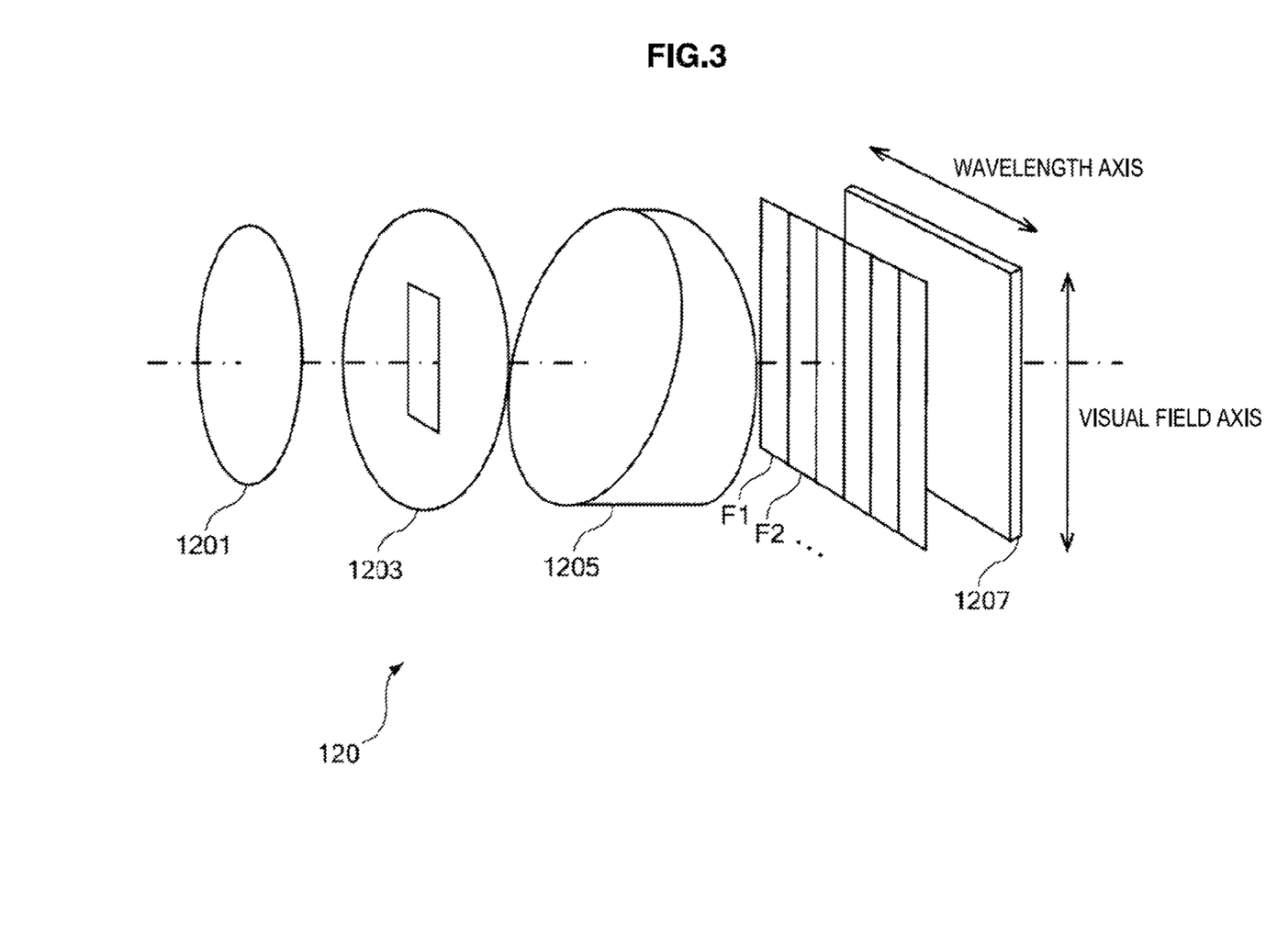
FIG. 3 is an illustration showing a configuration example of a light-reception unit of the biometric device according to the first embodiment of the present disclosure.
Figure 4:
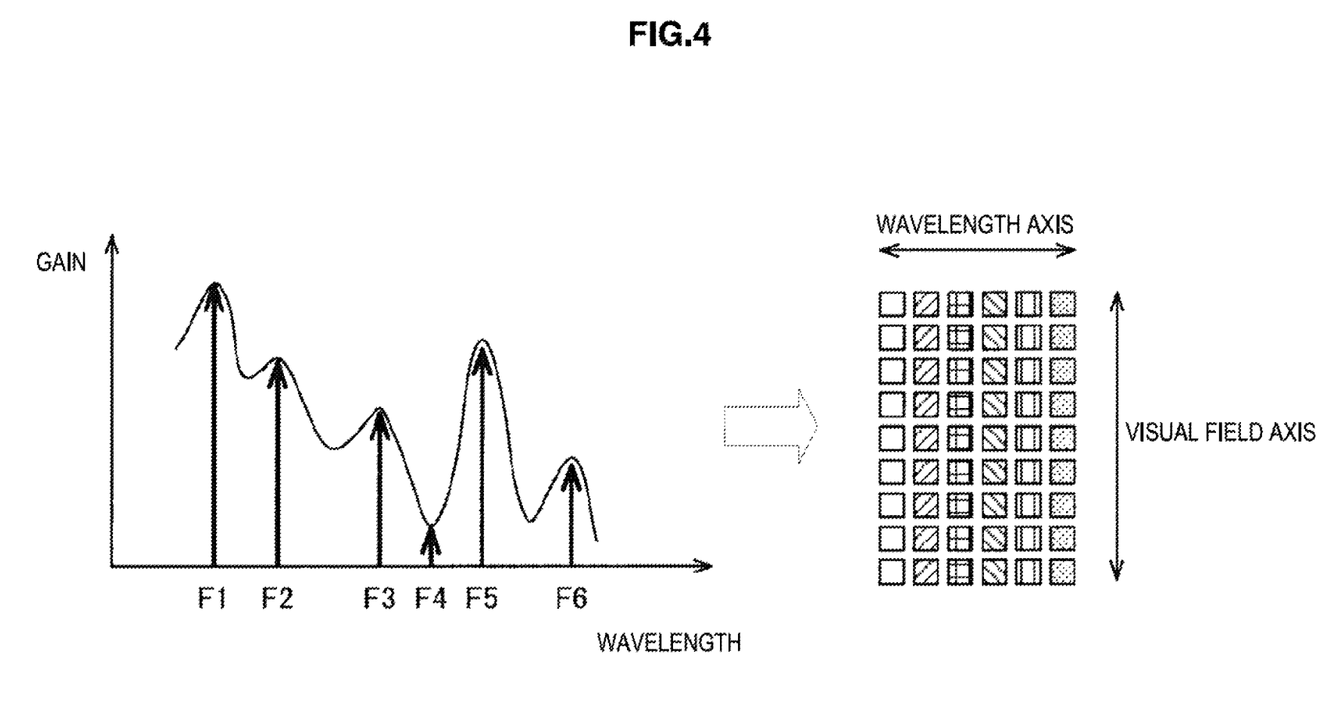
FIG. 4 is an illustration showing a configuration example of a filter in the first embodiment of the present disclosure.

First, a first embodiment of the present disclosure will be described, with reference to FIG. 2 to FIG. 4. FIG. 2 is an illustration showing a configuration of a biometric device according to a first embodiment of the present disclosure. FIG. 3 is an illustration showing a configuration example of a light-reception unit of the biometric device according to the first embodiment of the present disclosure. FIG. 4 is an illustration showing a configuration example of a filter in the first embodiment of the present disclosure.

With reference to FIG. 2, the biometric device 100 includes a light source unit 110, a light shield 112, a light-reception unit 120, a filter 122, an analysis unit 130, and a control unit 140. The biometric device 100 is a biometric device which performs biometric measurements using the fluorescence spectroscopy.

The light source unit 110 is arranged facing a first part on a surface of an organism B and irradiates this part with excitation light E. Here, the excitation light E is light for placing a body substance T of the organism B in an excited state to cause it to emit fluorescence light. Specifically, after absorbing the excitation light E and becoming the excited state, the body substance T of the organism B emits the fluorescence light F and returns to a ground state. While ultraviolet rays or visible rays of short wavelengths, for example, are used as such excitation light E, which is not limited to this, and light of any wavelength can be used as far as it is light that can place a substance in the body into an excited state. As the light source unit 110, for example, a light emitting diode (LED: Light Emitting Diode) or a small-size laser and the like is used.

The light-reception unit 120 is arranged facing a second part on the surface of the organism B and receives fluorescence light emitted from this part. The light-reception unit 120 converts the fluorescence light received with a photo detector (PD: Photo Detector) and the like into an electric signal, and supplies it to the analysis unit 130. Here, the second part on the surface of the organism B is a part adjacent to the first part where the light source unit 110 is arranged. In addition, the fluorescence light emitted from the second part is light emitted from the body substance T of the organism B which became the excited state by the excitation light E.

Such a light-reception unit 120 will be further described with reference to FIG. 3. With reference to FIG. 3, the light-reception unit 120 includes a two-dimensional spectroscope having a lens 1201, a slit 1203, a prism 1205, and an imaging device 1207. As the imaging device 1207, a photodiode, or a two-dimensional image sensor of CCD (Charge Coupled Device) type, CMOS (Complementary Metal Oxide Semiconductor) type or TFT (Thin Film Transistor) type and the like is used, for example. Light guided by the lens 1201 and the slit 1203 is dispersed by the prism 1205 to form a two-dimensional image having one side as a wavelength axis and the other as a visual field axis on the imaging device 1207. Such a configuration enables detection of a change due to a position of a spectral component, for example.

With this, data of a singular point present in a measurement target range, for example, can be corrected or deleted. The organism B has a part where is present an element that affects a measurement result, such as skin hair, a bruise or a mole on the surface, or a blood vessel of an artery or a vein in the body and the like, for example. It is believed that in such a part, a spectrum becomes discontinuous along the visual field axis. Therefore, with the configuration of the light-reception unit 120 described above, such a part can be detected as a singular point and a more accurate measurement result can be obtained even without selecting a measurement position by visual inspection or acquiring an average value through more than one measurement. In addition, a person who makes measurements may be notified audibly or by display and the like of whether or not a current measurement site is appropriate, based on flatness of measured volume thus measured. Note that the configuration of the light-reception unit 12 is not limited to the above example and may be a configuration using a line sensor, for example.

In addition, as shown in FIG. 3, filters F1 to F6 may be provided in the light-reception unit 120. In the shown example, the filters F1 to F6 are narrowband filters divided in a direction of the wavelength axis of the image formed on the imaging device 1207, each being specialized in a different wavelength. This enables light of each wavelength to be individually measured in the direction of the wavelength axis. In addition, as shown in FIG. 4, the filters F1 to F6 may be a narrowband filter such as an RGB filter which corresponds to a group of wavelengths to explore. In this case, the prism 1205 can be omitted, and with this, the light-reception unit 120 can be downsized and optical components used in the biometric unit 100 can also be reduced Here, in this embodiment, the light source unit 110 and the light-reception unit 120 are arranged facing separate parts on the surface of the organism B, as described above. Specifically, in this embodiment, unlike the case of the related art as described above, on the surface of the organism B, a part which excitation light E is entered differs from a part where fluorescence light subject to measurement is emitted. As shown, such a configuration is enabled by use of the property that the excitation light E is scattered after entering the inside of the organism B. The excitation light entering from a first part on the surface of the organism B where the light source unit 110 is arranged is scattered within the organism B, and reaches a body substance T lying in a second part, for example. With this, the body substance T is excited to emit the fluorescence light F. This fluorescence light F is emitted from the second part, and received by the light-reception unit 120.

Thus, in this embodiment, since the light source unit 110 and the light-reception unit 120 may apply the excitation light E or receive the fluorescence light F at separate parts on the surface of the organism B, there is no need for a space between the light source unit and the light-reception unit and the surface of the organism B which was needed in the case of the related art described above. Therefore, the biometric device 100 according to this embodiment can be downsized, when compared with, for example, the biometric device 10 according to the related art described above.

In addition, in this embodiment, since the space between the light source unit 110 and the surface of the organism B can be eliminated, specifically, the light source unit 110 can be arranged in proximity to the surface of the organism B, the efficiency of applying the excitation light E into the organism B can be improved. In addition, in the biometric device 100, the light-reception unit 120 can also be arranged in proximity to the surface of the organism. This enables efficient collection of weak fluorescence light emitted from the surface of the organism.

The light shield 112 is arranged between the light source unit 110 and the light-reception unit 120. The light shield 112 prevents the excitation light applied from the light source unit 110, for example, from entering the side of the light-reception unit 120 immediately or after being reflected on the surface of the organism B. As described above, in this embodiment, since on the surface of the organism B, the part to which the excitation light E is applied differs from the part where the fluorescence light subject to measurement is emitted, the excitation light E and the fluorescence light can be isolated by provision of the light shield 112. This reduces the excitation light E which is received by the light-reception unit 120 and affects analysis results of the fluorescence light F and improves an S/N (Signal/Noise) ratio, which can consequently improve precision of the analysis of the fluorescence light F.

The filter 122 is an optical filter arranged between the organism B and the light-reception unit 120. The filter 122 can be a narrowband bandpass filter that lets light of the wavelength of inspection light, specifically, the fluorescence light F pass, while not letting light of the wavelength of the excitation light E pass. Provision of the filter 11 can prevent reception by the light-reception unit 120 of the excitation light E which is scattered within the organism B and emitted from the surface of the organism B without reaching the body substance T. Similar to the case of the light shield 112, this reduces the excitation light E received by the light-reception unit 120 and affecting the analysis results of the fluorescence light F, which can improve precision of the analysis of the fluorescence light F.

The analysis unit 130 is implemented by a computer having a CPU (Central Processing Unit), a RAM (Random Access Memory), a ROM (Read Only Memory) and the like, for example. The analysis unit 130 analyzes a spectrum or intensity of fluorescence light F based on data of the fluorescence light F acquired from the light-reception unit 120. With this, the body substance T of the organism B which emitted the fluorescence light F, for example, can be quantified. The analysis unit 130 may be a part of the biometric device 100 or an external device to be connected to the biometric device 100. In addition, imaging data of the fluorescence light F generated by the light-reception unit 120 is stored in a removable storage medium, which is then removed from the biometric device 100 and connected to other device having an analysis unit 130, so that the data of the fluorescence light F may be analyzed.

Here, in analysis of the fluorescence light F, the analysis unit 130 may perform additional processing which conforms to measurement of the body substance T of the organism B. For example, the analysis unit 130 may separate fluorescence light emitted by a substance in arterial blood from received fluorescence light, with the principle similar to a pulse oximeter. In this case, of the fluorescence light F, for example, the analysis unit 130 may separate a component which varies with time, as that due to a pulse of the artery.

The control unit 140 is implemented by a computer having a CPU, a RAM, a ROM and the like, for example. The control unit 140 controls operation of each unit of the aforementioned biometric device 100. For example, the control unit 140 controls operation of the aforementioned light source unit 110 and the light-reception unit 120.

2-2. Second Embodiment

Figure 5:
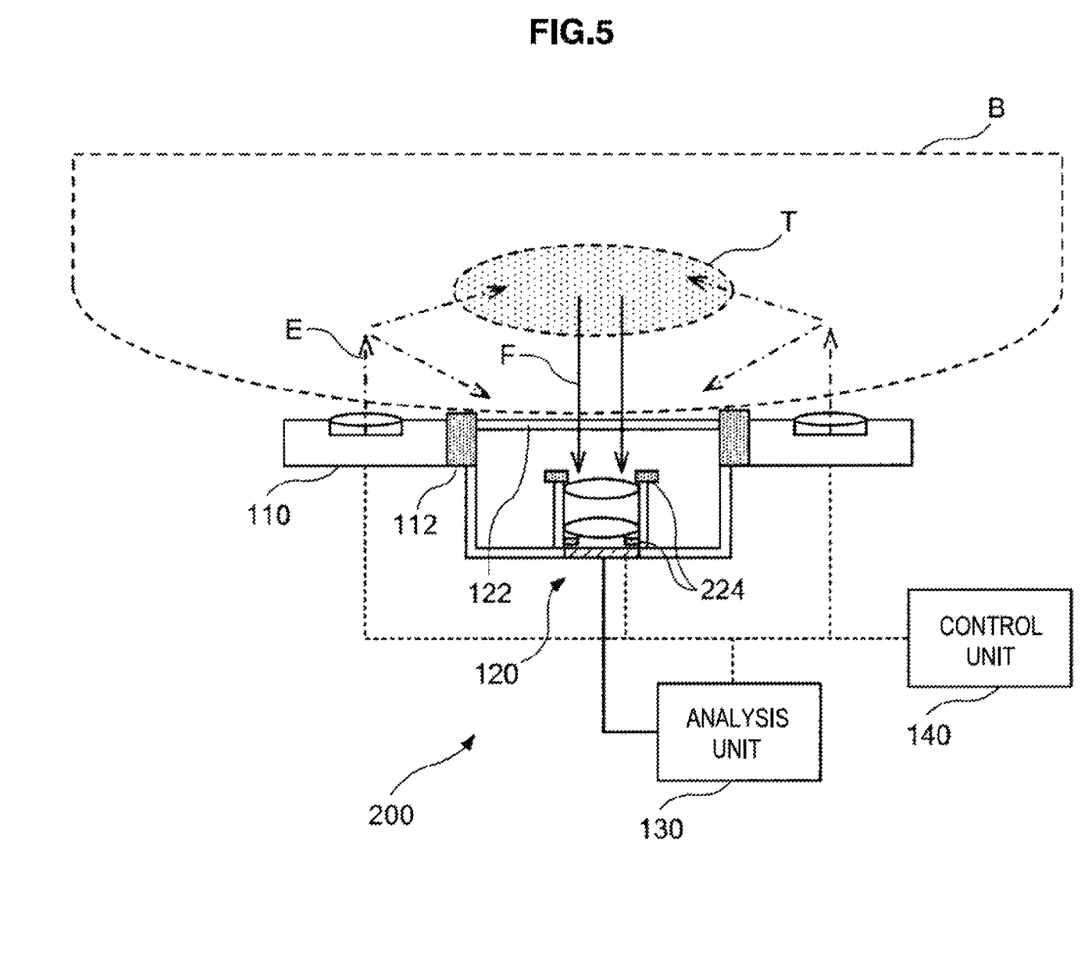
FIG. 5 is an illustration showing an example of using a line sensor for a light-reception unit in the second embodiment of the present disclosure.

A second embodiment of the present disclosure will be described hereinafter, with reference to FIG. 5. FIG. 5 is an illustration showing a configuration of a biometric device according to the second embodiment of the present disclosure.

With reference to FIG. 5, a biometric device 200 includes a light source unit 210, a light shield 112, a light-reception unit 120, a filter 122, a diaphragm 224, an analysis unit 130, and a control unit 140. Note that since of the aforementioned components, those other than the diaphragm 224 can have a similar configuration to the first embodiment described above, and thus a detailed description will be omitted.

The diaphragm 224 is an optical member for limiting directionality of light entering the light-reception unit 120. The diaphragm 224 selectively lets fluorescence light F in a direction perpendicular to an organism B, for example, pass and enter the light-reception unit 120. This can prevent mixing of the fluorescence light F emitted from, for example, any part other than a measurement target part. As an optical member for limiting directionality of the fluorescence light F entering the light-reception unit 120, not only the diaphragm 224 but also a light shield may be used, for example.

In addition, as other configuration for preventing any light other than the fluorescence light F from entering the light-reception unit 120, a microlens array may be provided, for example. The microlens array is a lens array of a plurality of small light-reception lenses having depth of field corresponding to depth of a body substance T from a surface of the organism B and being provided in an array, and guides the fluorescence light F entering the light-reception unit 120.

As in this embodiment, provision of an optical member for preventing any light other than the fluorescence light F entering the light-reception unit 120 prevents excitation light scattered in any part other than the body substance T subject to measurement or fluorescence light emitted by a body substance not subject to measurement from mixing into the fluorescence light F subject to measurement, thereby enabling improvement of precision in measurements.

2-3. Third Embodiment

Figure 6:
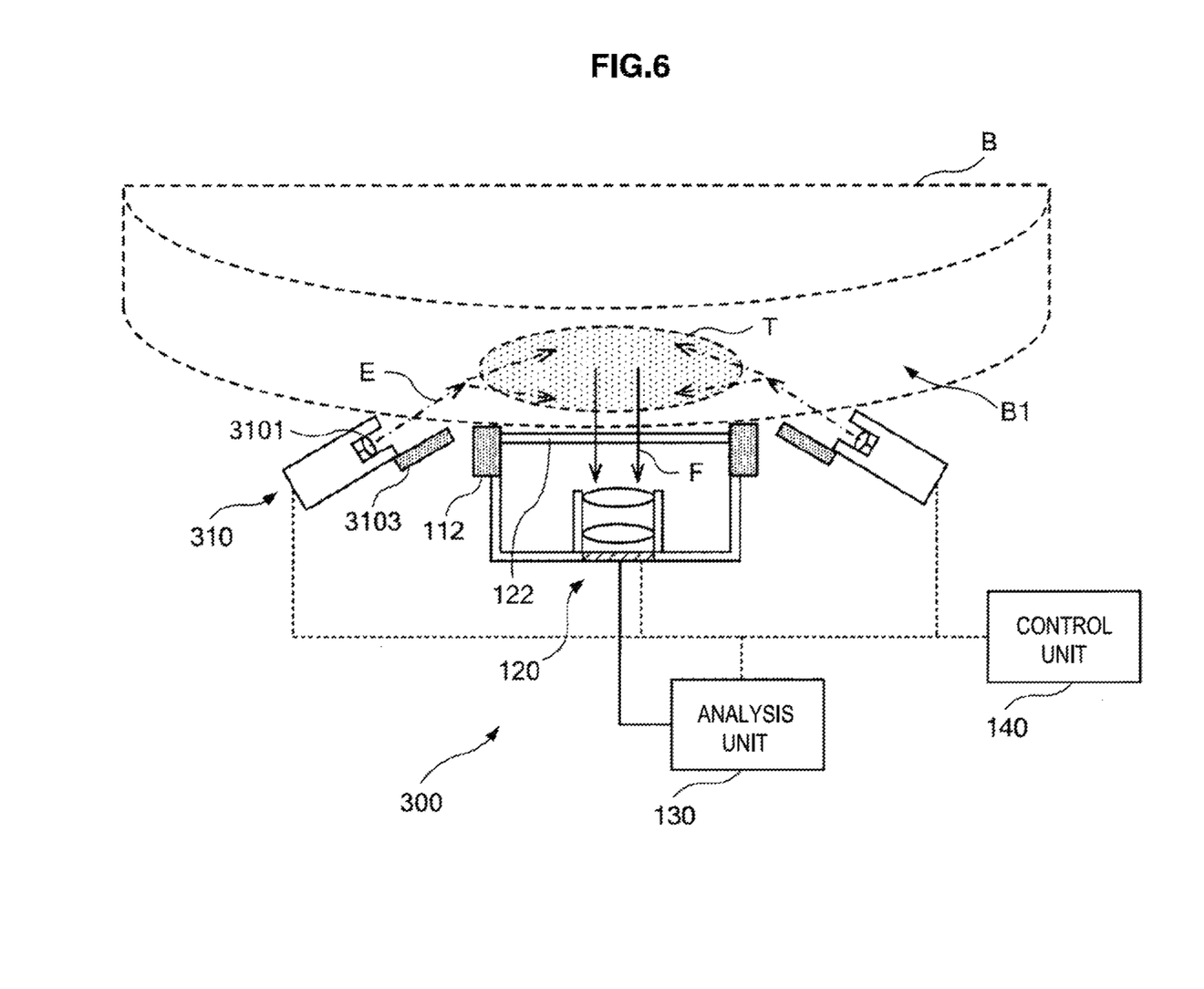
FIG. 6 is an illustration showing an example of using a line sensor for a light-reception unit in the third embodiment of the present disclosure.

A third embodiment of the present disclosure will be described hereinafter, with reference to FIG. 6. FIG. 6 is an illustration showing a configuration of a biometric device according to the third embodiment of the present disclosure.

With reference to FIG. 6, a biometric device 300 includes a light source unit 310, a light shield 112, a light-reception unit 120, a filter 122, an analysis unit 130, and a control unit 140. Note that since of the aforementioned components, those other than the light source unit 310 can have a similar configuration to the first embodiment described above, and thus a detailed description will be omitted. In addition, these components can have a similar configuration to the second embodiment described above.

The light source unit 310 is arranged facing a first part on a surface of an organism B, and irradiates this part with excitation light E. The light source unit 310 applies the excitation light E by using an LED and the like, for example. As a different point from the light source unit 110 of the first embodiment described above, the light source unit 310 applies the excitation light L in a direction inclined to the surface of the organism B. More specifically, the light source unit 310 applies the excitation light E in a direction inclined toward the light-reception unit 120. The light source unit 310 may have optics 3101 including one or more lens or diaphragm and the like to provide excitation light E to be applied with high directionality. In addition, the light source unit 310 may also have a light shield 3103 to prevent leakage of the excitation light E.

Such a configuration is effective when the biometric device 300 is specialized in measurements of a dermic layer of the organism B, for example. In this case, a body substance T subject to measurement lies in the dermic layer B1 close to the surface of the organism B. In order to effectively excite the body substance T by using the excitation light E, it is useful to incline a direction of application of the excitation light E and also to provide the excitation light E with directionality, thereby having more excitation light E reach the body substance T. By way of example, if the light-reception unit 120 is configured to receive fluorescence light F in a direction almost perpendicular to the surface of the organism B, the light source unit 310 may apply the excitation light E in a direction inclined to the extent that it is almost orthogonal to the direction of this fluorescence light F. The excitation light E and the fluorescence light F being almost orthogonal can prevent crosstalk with the excitation light E and the fluorescence light F, for example.

2-4. Fourth Embodiment

Figure 7:
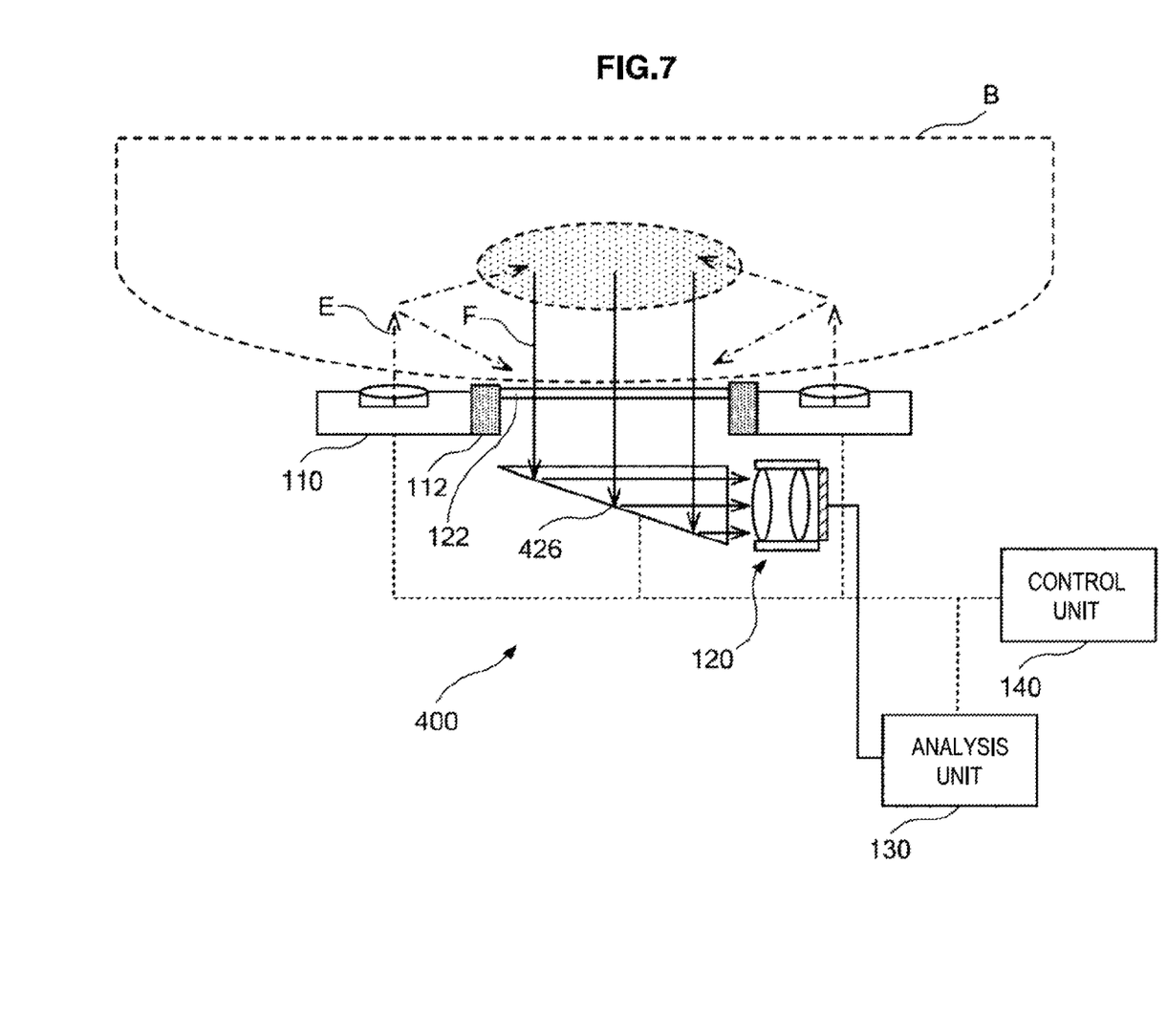
FIG. 7 is an illustration showing an example of using a line sensor for a light-reception unit in the fourth embodiment of the present disclosure.

A fourth embodiment of the present disclosure will be described hereinafter, with reference to FIG. 7. FIG. 7 is an illustration showing a configuration of a biometric device according to the fourth embodiment of the present disclosure.

With reference to FIG. 7, a biometric device 400 includes a light source unit 110, a light shield 112, a light-reception unit 120, a filter 122, a light-collection prism 426, an analysis unit 130, and a control unit 140. Note that since of the aforementioned components, those other than the light-collection prism 426 can have a similar configuration to the first embodiment described above, and thus a detailed description will be omitted. In addition, these components can have a similar configuration to the second or third embodiment described above.

The light-collection prism 426 collects fluorescence light emitted from an organism to the light-reception unit 120. As shown, the light-collection prism 426 converges fluorescence light F emitted from a second region on a surface of an organism B and guides it to the light-reception unit 120. This eliminates the need for provision of the light-reception unit 120 sized to cover the entire second region, and the overall biometric device 400 can also be downsized by downsizing of the light-reception unit 120.

2-5. Fifth Embodiment

Figure 8:
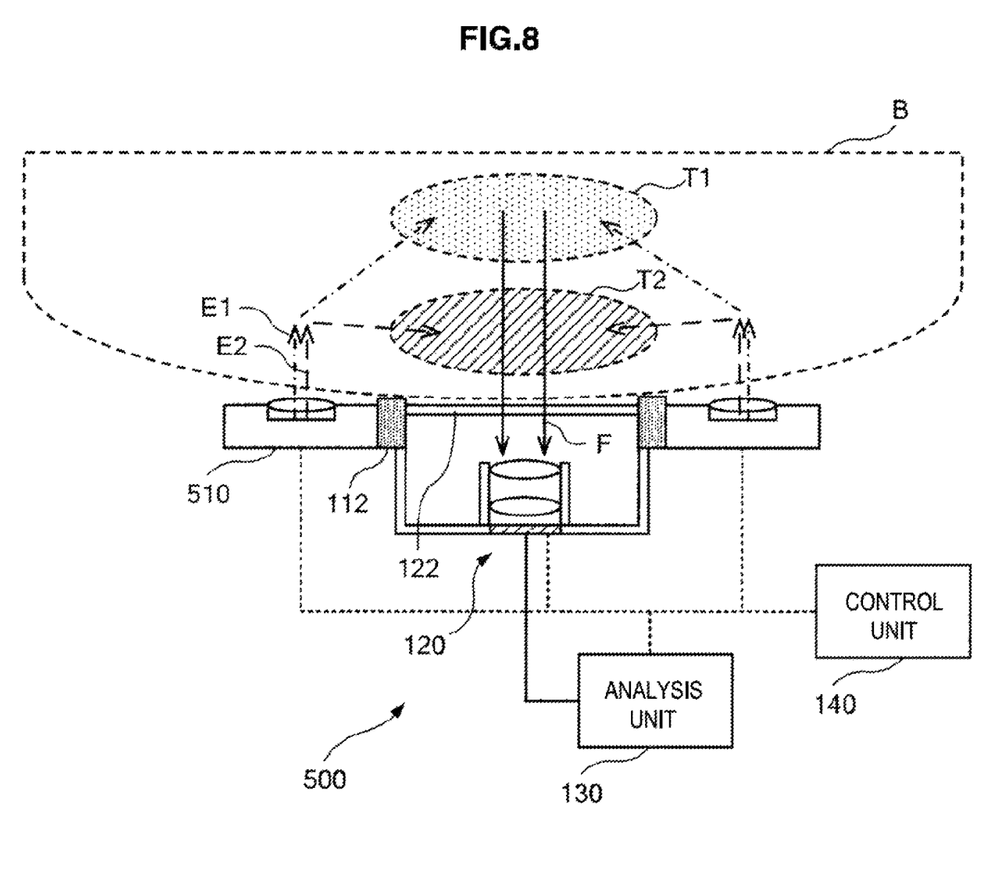
FIG. 8 is an illustration showing an example of using a line sensor for a light-reception unit in the fifth embodiment of the present disclosure.

A fifth embodiment of the present disclosure will be described hereinafter, with reference to FIG. 8. FIG. 8 is an illustration showing a configuration of a biometric device according to the fifth embodiment of the present disclosure.

With reference to FIG. 8, a biometric device 500 includes a light source unit 510, a light shield 112, a light-reception unit 120, a filter 122, an analysis unit 130, and a control unit 140. Note that since of the aforementioned components, those other than the light source unit 510 can have a similar configuration to the first embodiment described above, and thus a detailed description will be omitted. In addition, these components can have a similar configuration to any of the second to fourth embodiments described above.

The light source unit 510 is arranged facing a first part on a surface of an organism B, and irradiates this part with light by using an LED and the like, for example. Here, the light source unit 510 applies in time division manner excitation light E1 for exciting a body substance T1 of the organism B to cause it to emit fluorescence light F, and light E2 for measuring a body substance T2 which is different from the body substance T1 and having a wavelength which is different from the excitation light E1. The light E2 may be light for exciting the body substance T2 to cause it to emit fluorescence light similar to the excitation light E1, or light for measuring the body substance T2 with light absorptivity. The body substance T2 can be a measurement interfering substance to the body substance T1, for example.

For example, the light source unit 510 applies light having a wavelength of 940 nm as the light E2. In this case, since the wavelength of the light E2 is specific to light absorption by fat, an amount of fat in the organism B can be measured with the light E2. In addition, the light source unit 510 may also apply light having a wavelength of 568 nm, 660 nm, or 890 nm, as the light E2. In this case, since the wavelength of the light E2 is absorption wavelength specific to oxygenated hemoglobin, it is possible to use the light E2 to measure to what degree absorption by blood in the organism prevents the excitation light E1. In addition, the light source unit 510 may also apply light having a wavelength of 800 nm to 940 nm. In this case, since the wavelength of the light E2 is absorption wavelength specific to reduced hemoglobin, influence of components of arterial blood on fluorescence light can be measured.

Thus, by the light source unit 510 applying the excitation light E1 and the light E2 in time division manner, it is possible to measure a state of the fluorescence light F together with fat or blood which can be a measurement interfering substance to the fluorescence light F and to appropriately correct any fluctuation in measurement results caused by the fluorescence light F of the body substance T1 due to a change of these components.

In addition, for example, the light source unit 510 may apply in time division manner the excitation light E1 for exciting the body substance T1 and the light E2 for exciting the body substance T2. In this case, the excitation light E1 and the light E2 may be light having an excitation wavelength of each of the body substance T1 and the body substance T2. Both body substance T1 and the body substance T2 may also be a substance subject to measurement. Specifically, in this case, multiple body substances T1, T2 contained can be separately measured by exciting them with excitation light corresponding to each of them to cause them to emit fluorescence light.

3. SUPPLEMENT

The embodiments of the present disclosure have been described above. According to these embodiments, size of a biometric device, for example, can be reduced. By way of example, while size of the biometric device according to the related art as shown in FIG. 1 has hundreds of $cm^3$, it is possible to reduce size of the biometric device according to the embodiments of the present disclosure to a few $cm^3$ to tens of $cm^3$.

In addition, in a certain embodiment of the present disclosure, by arrangement of a light source unit applying excitation light in proximity to a surface of an organism, irradiation power of the light source is reduced and consumed power can be reduced, while ensuring an amount of excitation light which is enough to obtain sufficient fluorescence light. In addition, with this, if excitation light is ultraviolet rays, for example, influence of the excitation light on a human body can be reduced.

In addition, in a certain embodiment of the present disclosure, by diffusing excitation light within an organism and letting it reach a body substance, it is possible to reduce excitation light which is reflected on a surface of the organism and mixes into fluorescence light and to improve precision of measurement results with the fluorescence light.

In addition, in a certain embodiment of the present disclosure, by separation of a part to which excitation light is applied from a part where fluorescence light is emitted on a surface of an organism, interference with the excitation light and the fluorescence light in the vicinity of the surface of the organism can be reduced, when a substance for which wavelength of excitation light and that of fluorescence light are close is measured, for example.

In addition, in a certain embodiment of the present disclosure, by applying light for inspection in time division manner with excitation light to measure a measurement interfering substance in an organism, it is possible to reduce a change or error of a measured value due to a constitutional difference of organisms.

(Hardware Configuration)

Figure 9:
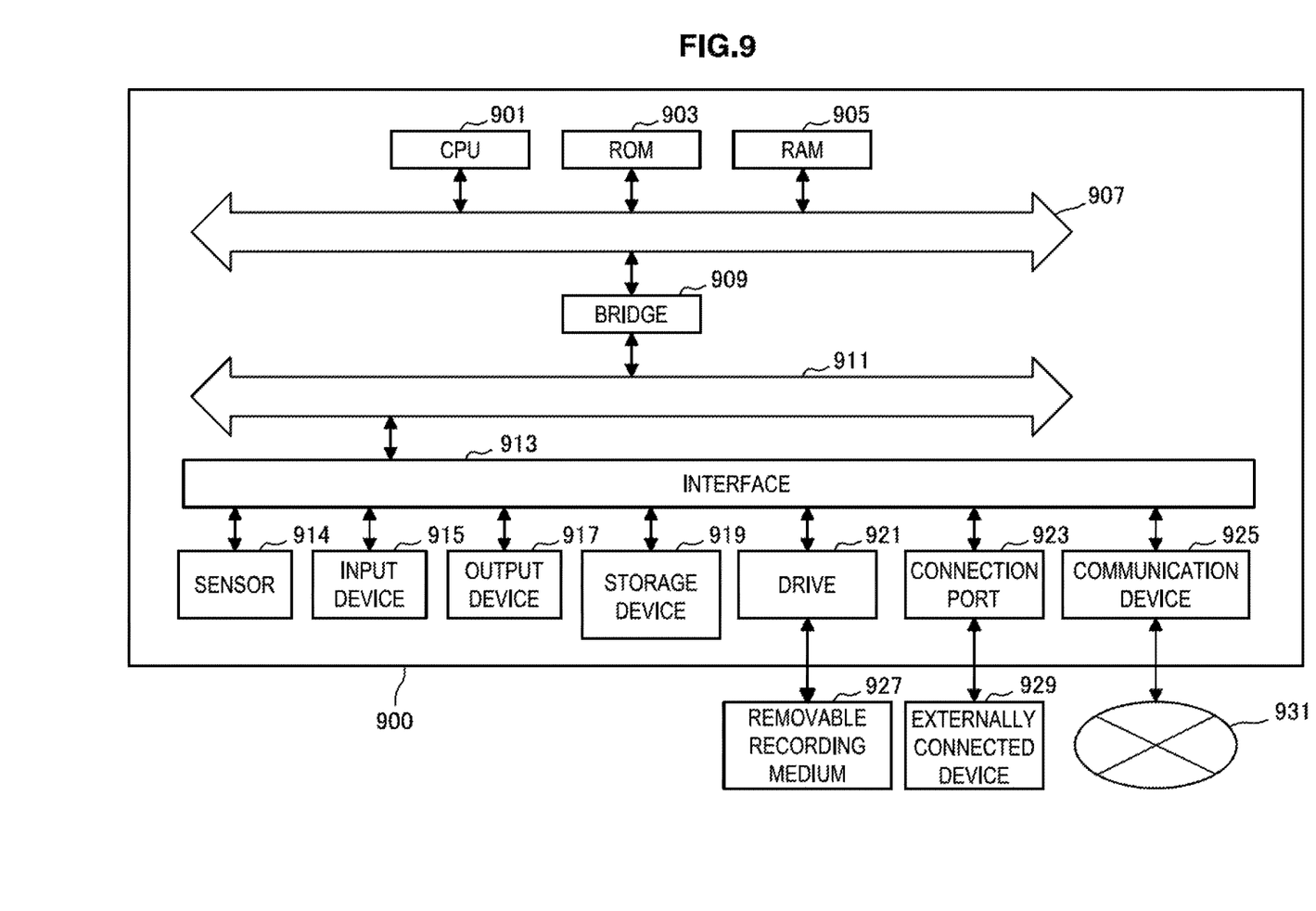
FIG. 9 is a block diagram for illustrating a hardware configuration of an information processor.

A hardware configuration of an information processor 900 capable of implementing a biometric device according to the embodiments of the present disclosure will be described hereinafter in detail with reference to FIG. 9. FIG. 9 is a block diagram for describing the hardware configuration of the information processor 900 according to the embodiments of the present disclosure.

The information processor 900 mainly includes a CPU 901, a ROM 903, and a RAM 905. In addition, the information processor 900 further includes a host bus 907, a bridge 909, an external bus 911, an interface 913, a sensor 914, an input device 915, an output device 917, a storage device 919, a drive 921, a connection port 923 and a communication device 925.

The CPU 901 acts as an arithmetic processing unit and a control device, and controls behavior in the information processor 900, in general, or a part thereof, according to various programs recorded in the ROM 903, the RAM 905, the storage device 919, or a removable recording medium 927. The ROM 903 stores a program or an arithmetic parameter and the like to be used by the CPU 901. The RAM 905 primarily stores a program to be used by the CPU 901 or a parameter which changes as appropriate in execution of the program, and the like. These are interconnected by the host bus 907 constituted of an internal bus such as a CPU bus and the like.

The host bus 907 is connected with the external bus 911 such as a PCI (Peripheral Component Interconnect/Interface) bus by way of the bridge 909.

The sensor 914 is detecting means for detecting biological information unique to a user or various types of information to be used to acquire such biological information. This sensor 914 includes, for example, various imaging devices such as a CCD (Charge Coupled Device) or a CMOS (Complementary Metal Oxide Semiconductor) and the like. In addition, the sensor 914 may further have optics such as a lens to be used to image an organism site or a light source and the like. The sensor 914 may also be a microphone and the like for acquiring sound and the like. Note that in addition to those mentioned above, the sensor 914 may also include various measuring instruments such as a thermometer, an illuminometer, a hygrometer, a speedometer, an accelerometer, and the like.

The input device 915 is an operational tool for a user to operate, such as a mouse, a keyboard, a touch panel, a button, a switch, and a lever, for example. The input device 915 may also be remote control means utilizing infrared rays or other electric wave or an externally connected device 929, such as a mobile phone or a PDA and the like, which responds to operation of the information processor 900. Furthermore, the input device 915 is constituted of an input control circuit and the like generating an input signal based on information which a user enters by using the aforementioned operational tool and outputting it to the CPU 901. By operating this input device 915, the user of the information processor 900 can input various types of data in the information processor 900 or give an instruction on processing operation.

The output device 917 is constituted of a device capable of visually or audibly informing the user of acquired information. Such a device includes a display device such as a CRT display unit, a liquid crystal display unit, a plasma display unit, an EL display unit, and a lamp and the like, or a voice output device such as a speaker and a headphone and the like, a printer unit, a mobile phone, a facsimile and the like. The output device 917 outputs a result obtained from various types of processing performed by the information processor 900, for example. Specifically, the display device displays the result obtained from the various types of processing performed by the information processor 900 in a text or an image. On the other hand, the audio output device converts an audio signal consisting of reproduced audio data or sound data and the like into an analog signal and outputs it.

The storage device 919 is a device for data storage configured as an example of a storage unit of the information processor 900. The storage device 919 is constituted of a magnetic storage unit device such as an HDD (Hard Disk Drive), a semiconductor storage device, an optical storage device, or a magneto-optical storage device and the like. This storage device 919 stores a program to be executed by the CPU 901 or various types of data, and various types of data acquired from the external, and the like.

The drive 921 is a reader-writer for a recording medium, and built in or externally mounted to the information processor 900. The drive 921 reads out information recorded in a mounted magnetic disk, optical disk or magneto-optical disk, or the removable recording medium 927 such as a semiconductor memory and the like, and outputs the information to the RAM 905. The drive 921 can also write a record in the mounted magnetic disk, optical disk or magneto-optical disk, or the removable recording medium 927 such as the semiconductor memory and the like. The removable recording medium 927 is, for example, a DVD medium, an HD-DVD medium, a Blu-ray medium and the like. The removable recording medium 927 may also be Compact Flash (Registered Trademark) (CompactFlash: CF), a flash memory or an SD memory card (Secure Digital memory card) and the like. In addition, the removable recording medium 927 may be an IC card (Integrated Circuit card) with a non-contact IC chip mounted or an electronic device and the like.

The connection port 923 is a port for directly connecting equipment to the information processor 900. By way of example, the connection port 923 includes a USB (Universal Serial Bus) port, an IEEE 1394 port, an SCSI (Small Computer System Interface) port and the like. As another example, the connection port 923 includes an RS-232C port, an optical audio terminal, an HDMI (High-Definition Multimedia Interface) port, and the like. By connecting the externally connected device 929 to this connection port 923, the information processor 900 directly acquires various types of data from the externally connected device 929 or provides the externally connected device 929 with various types of data.

The communication device 925 is a communication interface constituted of a communication device for connecting to a communication network 931, for example. The communication device 925 may be, for example, a communication card for a wired or wireless LAN (Local Area Network), Bluetooth (Registered Trademark), or WUSB (Wireless USB), and the like. In addition, the communication device 925 may be a router for optical communications, a router for ADSL (Asymmetric Digital Subscriber Line), or a modem for various types of communications and the like. This communication device 925 can send and receive a signal and the like to and from Internet or other communication devices, according to a predetermined protocol such as TCP/IP, for example. In addition, the communication network 931 connected to the communication device 925 is constituted of a network and the like connected by cable or wirelessly, and may be, for example, Internet, Home LAN, infrared communication, radio wave communication or satellite communication and the like.

As described above, one example of the hardware configuration which can implement capabilities of the information processor 900 according to the embodiments of the present disclosure has been shown. Respective components described above may be configured by the use of general-purpose members or may be configured by hardware specialized in the capabilities of the respective components. Therefore, it is possible to change a hardware configuration to utilize, as appropriate, depending on a technological level of when the embodiments are implemented.

The preferred embodiments of the present invention have been described above with reference to the accompanying drawings, whilst the technical scope of the present disclosure is not limited to the above examples, of course. It is obvious that a person skilled in the art may find various alterations and modifications within the technical ideas of the appended claims, and it should be understood that they will naturally come under the technical scope of the present invention.

Additionally, the present technology may also be configured as below.

(1)
A biometric device including:
a light source unit arranged facing a first part on a surface of an organism and configured to irradiate the first part with excitation light; and
a light-reception unit arranged facing a second part adjacent to the first part on the surface of the organism and configured to receive fluorescence light which is generated by the excitation light exciting a first body substance of the organism and emitted from the second part.

(2)
The biometric device according to (1), wherein the light source unit applies the excitation light in a direction inclined to the surface of the organism.

(3)
The biometric device according to (2),
wherein the light-reception unit receives the fluorescence light in a direction substantially perpendicular to the surface of the organism, and
wherein a direction in which the excitation light is applied is substantially orthogonal to the direction of the fluorescence light.

(4)
The biometric device according to any one of (1) to (3), further including:
an optical member configured to control directionality of light entering the light-reception unit.

(5)
The biometric device according to any one of (1) to (4), further including:
a lens array having a plurality of light-reception lenses arranged thereon in an array, the plurality of light-reception lenses having depth of field corresponding to depth of the first body substance from the surface of the organism and being provided in an array,
wherein the fluorescence light entering the light-reception unit is guided by the lens array.

(6)
The biometric device according to any one of (1) to (5), further including:
a light shield arranged between the light source unit and the light-reception unit.

(7)
The biometric device according to any one of (1) to (6), wherein the light source unit irradiates the first part in time division manner with the excitation light and light for measuring a second body substance which is different from the first body substance of the organism, the light having a wavelength which is different from a wavelength of the excitation light.

(8)
The biometric device according to any one of (1) to (7), wherein the light-reception unit includes a two-dimensional spectroscope.

(9)
The biometric device according to any one of (1) to (8), further including:
a light-collection unit configured to converge the fluorescence light and to guide the fluorescence light to the light-reception unit.

(10)
A biometric method including:
irradiating a first part on a surface of an organism with excitation light; and
receiving fluorescence light which is generated by the excitation light exciting a first body substance of the organism and emitted from a second part adjacent to the first part on the surface of the organism.

(11)
A program for causing a computer included in a biometric device including a light source unit and a light-reception unit to implement:
a function of controlling the light source unit; and
a function of controlling the light-reception unit, the light source unit being arranged facing a first part on a surface of an organism and being configured to irradiate the first part with excitation light, the light-reception unit being arranged facing a second part adjacent to the first part on the surface of the organism and being configured to receive fluorescence light which is generated by the excitation light exciting a first body substance of the organism and emitted from the second part.

(12)
A computer-readable recording medium having a program recorded thereon, the program causing a computer included in a biometric device including a light source unit and a light-reception unit to implement
a function of controlling the light source unit, and
a function of controlling the light-reception unit, the light source unit being arranged facing a first part on a surface of an organism and being configured to irradiate the first part with excitation light, the light-reception unit being arranged facing a second part adjacent to the first part on the surface of the organism and being configured to receive fluorescence light which is generated by the excitation light exciting a first body substance of the organism and emitted from the second part.

(13)
A biometric device including:
a light source unit arranged facing a first part on a surface of an organism and configured to apply excitation light in a direction inclined to the surface of the organism; and
a light-reception unit arranged facing a second part adjacent to the first part on the surface of the organism and configured to receive fluorescence light in a direction substantially perpendicular to the surface of the organism, the fluorescence light being generated by the excitation light exciting a first body substance of the organism and emitted from the second part,
wherein a direction in which the excitation light is applied is substantially orthogonal to the direction of the fluorescence light.

REFERENCE SIGNS LIST

100 biometric device
110 light source unit
112 light shield
120 light-reception unit
130 analysis unit
140 control unit
B organism
T body substance
E excitation light
F fluorescence light

The invention claimed is:
1. A biometric device comprising:
a light source unit configured to be positioned so as to face a first part on a surface of an organism and configured to irradiate the first part with excitation light;

a light-reception unit configured to be positioned so as to face a second part on the surface of the organism and configured to receive fluorescence light which is generated by the excitation light exciting a first body substance of the organism and emitted from the second part;

a light shield arranged between the light source unit and the light-reception unit and configured to prevent the excitation light from entering a side of the light-reception unit; and an optical filter configured to be arranged between the light-reception unit and the second part on the surface of the organism, the optical filter configured to allow the fluorescence light to pass to the light-reception unit while not allowing the excitation light to pass to the light-reception unit, the second part is adjacent to and separate from the first part such that the first part whereat the excitation light is irradiated is different from the second part whereat the fluorescence light is emitted, and the light source unit and the light-reception unit being positioned relative to each other so that when the biometric device is in use the first body substance of the organism is not in-line with the light source unit such that the excitation light irradiated from the light source unit reaches the first body substance after being scattered within the organism.

2. The biometric device according to claim 1, wherein the light source unit is configured to irradiate the first part in time division manner with the excitation light and light for measuring a second body substance which is different from the first body substance of the organism, the light having a wavelength which is different from a wavelength of the excitation light.

3. The biometric device according to claim 1, wherein the light-reception unit includes a two-dimensional spectroscope.

4. The biometric device according to claim 1, further comprising a diaphragm arranged to limit the fluorescence light which enters the light-reception unit to that having a predetermined direction relative to the second part of the surface of the organism to avoid the fluorescence light from a body substance other than from the first body substance from entering the light-reception unit.

5. A biometric method for use with a biometric device, said method comprising:

irradiating, by use of a light source, a first part on a surface of an organism with excitation light;

receiving, by use of a light reception unit, fluorescence light which is generated by the excitation light exciting a first body substance of the organism and emitted from a second part adjacent to the first part on the surface of the organism; and preventing, by use of a light shield arranged between the light source unit and the light-reception unit, the excitation light from entering a side of the light-reception unit; and allowing the fluorescence light to pass to the light reception unit while not allowing the excitation light to pass to the light reception unit, by use of an optical filter arranged between the light-reception unit and the second part on the surface of the organism, the second part is adjacent to and separate from the first part such that the first part whereat the excitation light is irradiated is different from the second part whereat the fluorescence light is emitted, and the light source unit and the light reception unit being positioned relative to each other so that the first body substance of the organism is not in-line with the light source unit such that the excitation light irradiated from the light source unit reaches the first body substance after being scattered within the organism.

6. The biometric method according to claim 5, further comprising limiting, by use of a diaphragm, the fluorescence light which enters the light-reception unit to that having a predetermined direction relative to the second part of the surface of the organism to avoid the fluorescence light from a body substance other than from the first body substance from entering the light-reception unit.

* * * * *